United States Patent [19]

Ender

[11] Patent Number: 4,768,504
[45] Date of Patent: Sep. 6, 1988

[54] DEVICE FOR OSTEOTOMY

[76] Inventor: Hans G. Ender, Krenngasse 3, Vienna, Austria, A-1180

[21] Appl. No.: 4,471

[22] PCT Filed: May 6, 1986

[86] PCT No.: PCT/AT86/00041
§ 371 Date: Dec. 17, 1986
§ 102(e) Date: Dec. 17, 1986

[87] PCT Pub. No.: WO86/06609
PCT Pub. Date: Nov. 20, 1986

[30] Foreign Application Priority Data

May 7, 1985 [AT] Austria ................................. 1368/85

[51] Int. Cl.⁴ ............................................. A61B 17/14
[52] U.S. Cl. ................................ 128/317; 128/92 VY; 30/166 A; 30/286
[58] Field of Search .................. 128/317, 310, 92 VD, 128/92 VJ, 92 VY, 92 VV, 92 VW; 30/166 A, 371, 372, 286, 289

[56] References Cited
U.S. PATENT DOCUMENTS 2,294,303  8/1942  Jagow ............................ 128/92 VD
4,273,117  6/1981  Neuhauser ...................... 128/310 X
4,284,080  8/1981  Rehder ................................ 128/305
4,509,511  4/1985  Neufeld .

FOREIGN PATENT DOCUMENTS 2304322 10/1976 France .

Primary Examiner—Michael H. Thaler
Attorney, Agent, or Firm—Holman & Stern

[57] ABSTRACT

A device for performing an osteotomy comprises an arcuately shaped saw blade (14), which in particular has a cross-sectional configuration in the shape of an arc of a circle, non-rotatably connected via a carrier body (12) with a spacer member (9) driven by an oscillating drive device (6) so that the saw blade (14) performs a reciprocating circular movement. A retractable guide bushing (21) is loaded by a spring (22) and slidably supported within the spacer member (9) so that it is resiliently urged in the feed direction (27) of the saw blade (14), the guide bushing (21) having a guide passage (26) accommodating a guide pin, for example a boring wire, anchored within the bone.

11 Claims, 3 Drawing Sheets

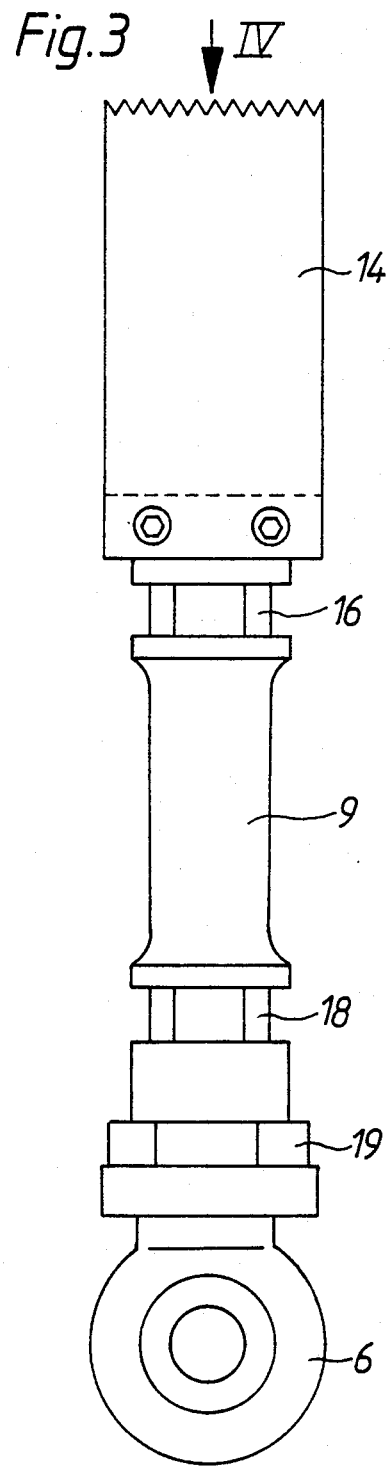
Fig. 3
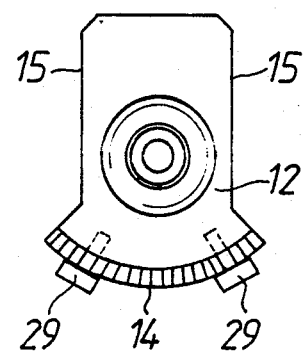
Fig. 4
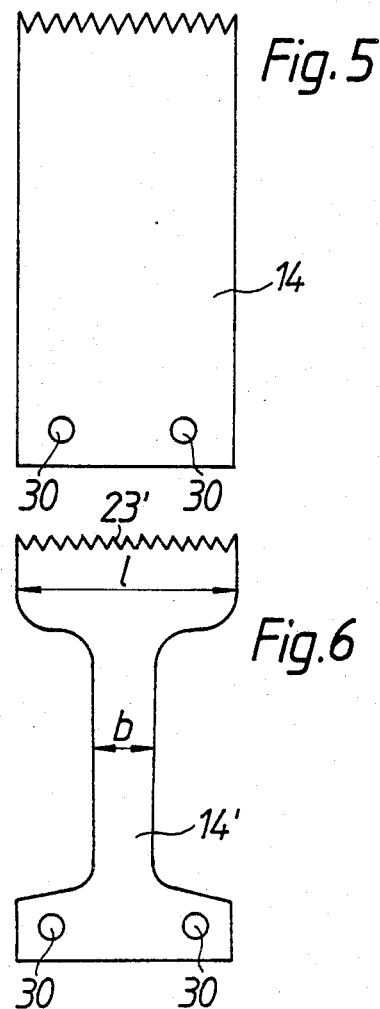
Fig. 5
Fig. 6

DEVICE FOR OSTEOTOMY

BACKGROUND OF THE INVENTION

1. Field of the Invention

This invention relates to a device for performing an osteotomy, of the type utilizing a saw blade driven by an oscillating drive means for performing a reciprocating movement of the saw edge.

2. Description of the Prior Art

There are already known various saws for performing an osteotomy, i.e. saws having a straight saw blade, saws having a saw blade with bent saw edge and also saws, in which the saw edge forms a closed circle. While both first-mentioned saw blades are mainly used for completely severing a bone, for example in case of an amputation, the last-mentioned saw blade is mainly used for withdrawing a piece of bone for examination.

The saws are either moved manually or by a drive means being, as a rule, pneumatically energized. In this connection, it is known to give to the saw blade a rotating movement or an oscillating movement.

The device according to the invention is mainly intended for a bone treatment in case of a wrongly healed bone fracture, i.e. if the bone fragments do not assume the correct relative position at the fracture area but include, for example, an angle one with the other in place of stretched position. In this case it is necessary to sever the bone at the area of the bone fracture and to adjust the thus obtained bone parts in the correct relative position, so that the fractured area may again heal in this correct position. It is important that both bone portions contact one another over as great a surface as possible, because the greater the contact surface between both bone portions the better and less troublesome is the healing.

If a correction shall be effected in case of a cured fraction area in which both bone portions do not assume the desired stretched position, but include one with the other a blunt angle, the procedure up till now was such that a wedge-shaped bone piece was cut out of the healed fractured area, the wedge being shaped such that positioning of both bone portions in the stretched position was possible. This known treating method results, however, in a plurality of drawbacks. For example, when cutting out a wedge, the total length of the bone will be reduced, which results, as a rule, also in functional drawbacks. Furthermore, it is very difficult to exactly determine the required wedge angle, on the one hand, and to cut out a wedge having this wedge angle, on the other hand. For obtaining a suitable contact between the bone portions adjusted along a straight line at the location of the cutting operation, which contact is required for the least troublesome healing process, it is frequently necessary to effect an additional cutting operation. Such additional cutting operation results, however, in a further reduction of the length of the bone. It is a further drawback that, also in case of an exact cut, the contact surface between both bone portions corresponds to the cross section of the bone and is thus approximately circular and in consequence comparatively small.

It is also known to give the contact area at the severed fractured area the shape of a V. The contact area is thus apparently increased, but in practice there result, however, only individual contact points, mainly because the roof-like protrusion of one of the bone portions does not exactly fit the V-shaped recess of the other bone portion when aligning the bone portions into the stretched position. In practice this results in a substantial reduction of the contacting surface, along which both bone portions actually contact one another. When applying this method, it is furthermore necessary to chisel the V-shaped impression out of one bone portion, which is extremely difficult and time-consuming and fequently results in shivering of the bone.

There is further known the so-called hexagonal osteotomy, in which the contacting surface has the shape of a partial contour of a polygon, which is cut out of the bone. Such a shape of the contacting surface can, however, only be produced with extreme difficulty and suffers furthermore from the drawback that the relative position of the bone portions can only be changed for a relative degree corresponding to the sector angle of the polygon, so that an exact adjustment of these bone portions in the desired position is not possible.

It is also known to give the contact area the shape of an arc. In this case, the procedure is such that holes are bored into the bone at narrow distances by means of a template, whereupon the bone webs between the holes are removed by means of a chisel. This procedure is extremely circumstantial. An exact arcuate contact surface can not be obtained in this manner.

BRIEF SUMMARY OF THE INVENTION

It is an object of the present invention to provide a device for performing an osteotomy avoiding the above mentioned drawbacks and producing between the bone portions a contact surface, which provides for an exact positioning of these bone portions in the desired position without any reduction of the length of the bone, and to reliably provide a great contact surface between both bone portions. It is a further object of the invention to provide the possibility to make a cut allowing continuous swivelling of the bone portions severed one from the other by the cut, so that the relative position of these bone portions can be exactly adjusted, noting that the contact surface is substantially greater than the circular contact surface corresponding to the bone cross section and obtained when effecting a straight cut, whereby the healing process is promoted. Furthermore, the saw blade is exactly guided during feeding for obtaining an unobjectionably guided cut. A spacer member not only provides the possibility for the arrangement of a guide passage for a guide pin attacked in the bone, but shall also reliably provides the distance between the saw blade and the drive means required for a comfortable operation.

If the position of the guide passage within the spacer member can not be changed, the guide passage can only assume a position in which it does not obstruct feeding of the saw blade. At the very beginning of the sawing operation a substantial portion of the guide pin anchored within the bone is not guided within the guide passage, so that the exactness of the guiding effect is impaired. For this reason, a guide bushing for the guide pin is conveniently arranged within the spacer member and protrudes in the one end position out of the spacer member and extends in the feed direction an amount equal to at least part of the length of the saw blade and is retractable within the spacer member against the force of a spring or the like resiliently urging it in the feed direction to the protruding position When retracted, at least part of its length is located within the interior of the spacer member. In this arrangement, the major part of the guide pin is guided within the guide bushing also at the very beginning of the sawing operation, so that an exact cut is reliably obtained in this stage. If, during the sawing operation, the front end of the guide bushing contacts the bone, the guide bushing is pushed back into the spacer member against the force of the spring or the like when further advancing the saw blade, so that the guide bushing does not obstruct further feeding advancement.

BRIEF DESCRIPTION OF THE DRAWINGS

The invention will now be described in detail with reference to the accompanying drawings showing examples of embodiment of the invention wherein:

FIG. 3 is an elevational view of the device according to the invention in direction of the arrow III in FIG. 2;

FIG. 4 is a view in direction of the arrow IV in FIG. 3.

FIG. 5 is an elevational view of an embodiment of a saw blade of a device according to the invention FIG. 6 is a view similar to FIG. 5 which shows a modified embodiment of such a saw blade.

DETAILED DESCRIPTION

Figure 1:
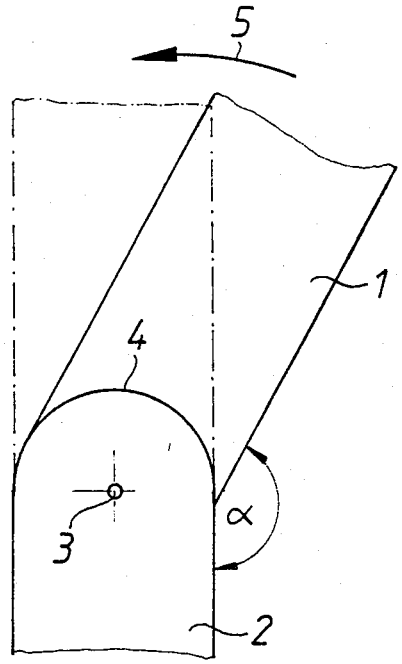
FIG. 1 is a schematic simplified representation of two healed bone portions including at the area of fracture in an undesired manner a blunt angle and further shows the configuration of the cut made by the inventive device for osteotomy.
Figure 2:
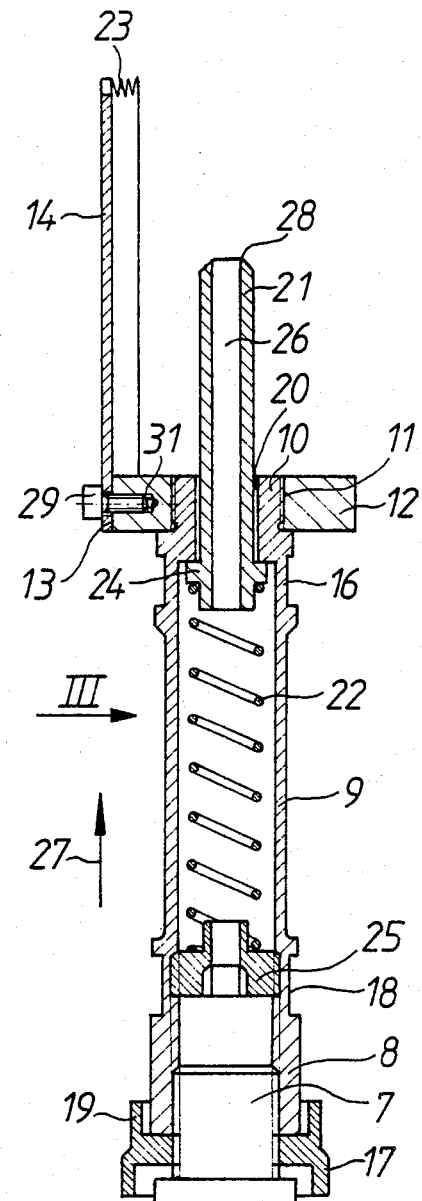
FIG. 2 is a longitudinal cross-sectional view through the device according to the invention.
Figure 7:
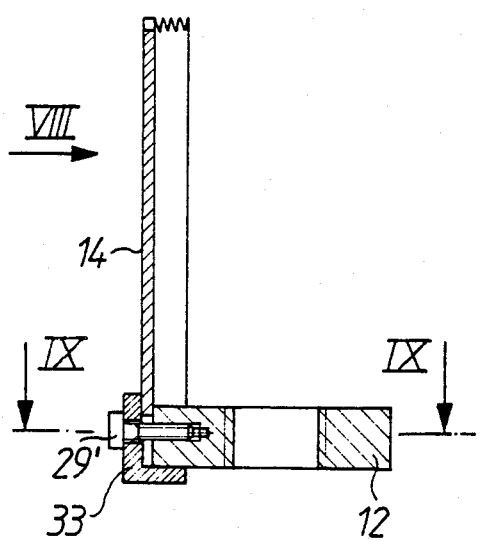
FIG. 7 is a cross-sectional view of an embodiment of a part for mounting the saw blade on the carrier body.
Figure 8:
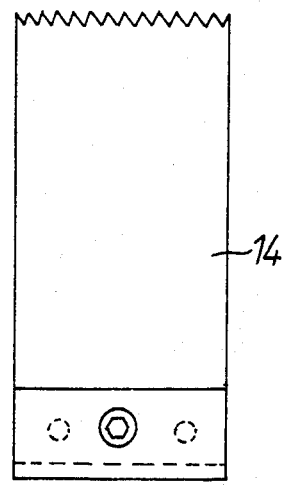
FIG. 8 is an elevational view in direction of the arrow VIII in FIG. 7.
Figure 9:
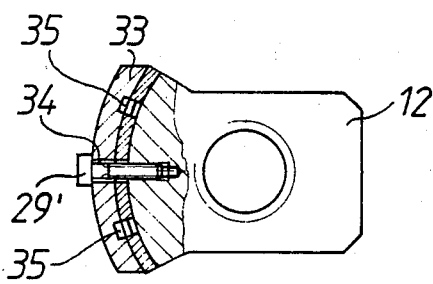
FIG. 9 is a cross-sectional view taken along line IX-IX in FIG. 7.
Figure 10:
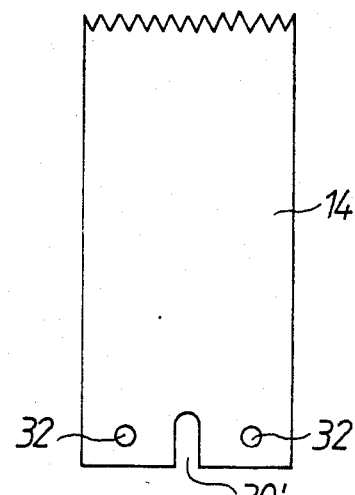
FIG. 10 is an elevational view of the saw blade used in the embodiment according to FIGS. 7 to 9 in demounted condition.

In FIG. 1, there are shown two bone portions 1, 2 healed at the area of fracture such that they include between them a blunt angle α. For effecting positioning in straight relation, shown in phantom the already healed area of fracture is severed by means of the inventive device for the osteotomy. For this purpose, a boring wire, for example a Steinman-pin, is bored into the bone at 3 and serves as a guide pin for the feeding movement for the saw blade as will be further explained during the subsequent description of the device according to the invention. The bone is severed by means of this saw blade, the configuration 4 of the cut being shown in this Figure. The bone portion 1 can then be swivelled in direction of the arrow 5 until it assumes the desired position shown in FIG. 1 in dash-dotted lines, in which position the bone portion 1 is fixed for the subsequent healing process. As can be taken from this Figure, swivelling can continuously be effected and the bone length is not reduced.

The device according to the invention has a gearing 6 which can be coupled with a known, preferably pneumatically energized, drive means, the drive pin 7 of which is provided with an external screw thread and performs an oscillating movement. A spacer member 9 is screwed onto the drive pin 7 by means of its internal threaded end 8. At the opposite end, the spacer 9 has an externally threaded pin 10 onto which a plate-like carrier body 12 is screwed by means of a threaded bore 11, an arcuately shaped saw blade 14 being fixed to the outer side wall 13 of carrier body 12. Such an arrangement provides for easy interchangeability of the saw blades 14, i.e. replacing worn saw blades with new saw blades, as well as replacing saw blades of greater curvature with saw blades of smaller curvature, and vice versa, respectively.

In particular, when using smaller saw blades 14 it is, however, advantageous for rapidly interchanging saw blades if the saw blade is, according to the invention, inseparably connected with the carrier body 12 and is thus interchanged together with the carrier body 12, but this embodiment is not shown in the drawing. For reliably establishing a non-rotatable connection between the spacer member 9 and the carrier body 12 it is necessary to firmly screw the threaded bore 11 of the carrier body 12, onto the threaded pin 10. To meet this requirement, the carrier body 12 has engaging surfaces 15 for a wrench and the spacer member 9 has at 16 a hexagonal cross section for a wrench, so that the spacer member 9 and the carrier body 12 can be rotated one relative to the other by means of these wrenches. It is, however, also possible that the pin 7 protruding from the spacer member 9 is connected with the bore 11 within the carrier body 12 by means of a bayonet catch.

A lock nut 17 cooperating with the front side of the threaded end 8 of the spacer member 9 is arranged on the threaded pin 7 to be in the position to non-rotatably connect the spacer member 9 with the threaded pin 7 of the drive means 6, on the one hand, and to allow for adjusting the desired relative position between the saw blade and the drive means 6, on the other hand. To provide for relative rotation between the end 8 and the lock nut 17 by means of wrenches, the spacer member 9 is provided with a further hexagonal part 18 for applying a wrench and the lock nut 17 is equally designed as a hexagonal nut at the area 19.

A bore 20 is provided within the threaded pin 10 of the spacer member 9 for guiding therein a guide bushing 21. This guide bushing is urged in the direction of the saw edge 23 of the saw blade 14 by means of a helical spring 22 located within the interior of the hollow spacer member until the flange 24 of this guide bushing 21 contacts the front surface of the cavity of the spacer member 9. The spring 22 is supported on an abutment 25 which is screwed into the thread within the end 8 of the spacer member 9. The passage 26 of the guide bushing 21 receives the guide pin anchored within the bone at the location 3 (see FIG. 1), so that the device according to the invention is guided during the feeding movement when performing the sawing operation in direction of the arrow 27, the saw edge 23 performing an oscillating movement and producing a cut corresponding to the cut line 4 shown in FIG. 1. As soon as the front surface 28 of the guide bushing 21 contacts the bone, this guide bushing is pushed against the force of the spring 22 into the cavity of the spacer member 9 during further advancing movement. An exact guiding effect for the device according to the invention is thus always reliably obtained by the guide pin inserted into the passage 26 of the guide bushing 21.

As can be seen in particular from FIG. 4, the saw blade 14 is arcuately shaped in a plane extending transversely to its feed direction, so that the blade is perfectly guided as required.

In the embodiment according to the FIGS. 2 to 5, the saw blade 14 is fixed to the side wall 13 of the carrier body 12 by means of two screws 29, which are passed through openings 30 in the saw blade 14 and are screwed into threaded bores 31 provided in the carrier body 12. Such an arrangement provides for interchanging a worn saw blade 14 without the necessity with a new blade for simultaneously also interchanging the carrier body 12. In the case of smaller saw blades, the saw blade 14 can, however, also be inseparably connected with the carrier body 12. When substituting a saw blade by a saw blade having another radius of curvature, the saw blade is conveniently interchanged together with the carrier body 12.

FIG. 6 shows an embodiment of a saw blade 14' in which the carrier body 12 can be connected with the part having the saw edge 23' via a web, said part being formed by a beam extending in transverse relation to the longitudinal direction of the web and having thus the shape of an axe. As can be taken from this Figure the length l of the saw edge 23' is substantially greater than the width b of the web located between the saw edge 23' and that end of the saw blade which is connected with the carrier body 12. A saw blade 14' of such construction is required if the bone area to be severed is covered by bands, sinews or the like, because the saw edge can then be applied below these bands and the desired configuration of cut can be obtained without hurting or damaging, respectively, the bands.

The FIGS. 7 to 10 show a further embodiment of the releasable mounting of the saw blade 14 on the carrier body 12. As can be taken from FIG. 10, the saw blade 14 has in its longitudinal axis an elongated slot 30' which is open in the direction of the edge of the saw blade adjacent the carrier body. Also there are provided holes 32. The saw blade 14 is fastened by means of a rail 33 of angular cross section and having a bore 34 aligned with the elongated slot 30' and accommodating a screw 29' screwed into the carrier body 12. Pins 35 protrude from the carrier body 12.

For the purpose of mounting the saw blade 14 on the side wall 13 of the carrier body 12, the screw 29' is unscrewed to such an extent that the rail 33 is lifted off the side wall 13 such that the saw blade 14 can be inserted into the interstice between the side wall 13 and protruding pins of the carrier body 12 and the rail 33. The shank of the screw is accommodated by the laterally open elongated slot 30'. When tightening the screw 29', the saw blade 14 is shifted relatively to the side wall 13 of the carrier body 12 where necessary to facilitate, the pins 35 entering the holes 32 and providing an additional fastening of the saw blade 14.

I claim:
1. A device for performing an osteotomy comprising:
   guide means adapted for anchoring on a bone adjacent to a position where the osteotomy is to be performed and projecting from said bone;
   a spacer member;
   oscillating drive means connected to said spacer member for rotating said spacer member in an oscillating rotary motion about an axis of rotation extending substantially in a feed direction toward the bone;
   a saw blade attached to and projecting from said spacer member for rotary oscillating movement therewith and having an arcuate cross-section in a plane therethrough extending substantially perpendicular to said axis of rotation;
   a guide bushing slidably mounted in said spacer member for movement in a direction substantially parallel to said axis of rotation and having a part thereof protruding from said spacer member in a direction parallel to said saw blade for a distance equal to at least part of but less than the length of said saw blade prior to use;
   spring means operatively engaging said guide bushing for resiliently urging said guide bushing in the protruding direction thereof; and
   a guide passage in said guide bushing having a central axis extending substantially coaxially with said axis of rotation for receiving said guide means therein in guiding relationship therewith so that said spacer member and saw blade are guided by said guide means in the feed direction during use and said guide bushing retracts into said spacer member.

2. A device as claimed in claim 1 wherein:
   said guide means comprises a boring wire bored into the bone.

3. A device as claimed in claim 1 and further comprising:
   a carrier body non-rotatably connected to said spacer member, said saw blade being connected to said carrier body; and
   a bore in said carrier body through which said guide bushing extends.

4. A device as claimed in claim 3 wherein:
   said guide means comprises a boring wire bored into the bone.

5. A device as claimed in claim 3 wherein said carrier body comprises:
   a plate-shaped member extending in a plane substantially perpendicular to said axis of rotation; and
   a side wall in said plate-shaped member;
   said saw blade having one end with a saw edge thereon and an opposite end connected to said side wall.

6. A device as claimed in claim 3 wherein:
   said saw blade is inseparably connected to said carrier body.

7. A device as claimed in claim 3 and further comprising:
   a pin element protruding from said spacer member surrounding said guide bushing and inserted into said bore in said carrier body.

8. A device as claimed in claim 7 and further comprising:
   an internal screw thread in said bore of said carrier body; and
   an external screw thread on said pin element engageable with said internal screw thread for fastening said carrier body on said spacer member.

9. A device as claimed in claim 7 and further comprising:
   cooperating bayonet fastening means on said pin element and said carrier body for releasably fastening said carrier body on said spacer element.

10. A device as claimed in claim 3 wherein said saw blade comprises:
    a beam part having a saw edge thereon; and
    a web part having one end connected to said beam part, and an opposite end connected adjacent thereto to said carrier body, and having a longitudinal axis extending substantially parallel to said axis of rotation;
    said beam part being connected to said web part in spaced relation to said carrier body and extending substantially transversely to said longitudinal axis of said web part.

* * * * *